US00PP18660P2

(12) United States Plant Patent
Tuite

(10) Patent No.: US PP18,660 P2
(45) Date of Patent: Mar. 25, 2008

(54) ***PHYSOCARPUS* PLANT NAMED 'LADY IN RED'**

(50) Latin Name: *Physocarpus opulifolius*
Varietal Denomination: Lady In Red

(76) Inventor: Jonathan Tuite, West Acre Gardens, King's Lynn (GB), PE32 1UJ ( * ) Notice: Subject to any disclaimer, the term of this patent is extended or adjusted under 35 U.S.C. 154(b) by 20 days.

(21) Appl. No.: 11/523,298

(22) Filed: Sep. 18, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para

(57) ABSTRACT

A new cultivar of *Physocarpus* plant named 'Lady in Red' that is characterized by freely branching habit, red foliage and pink flowers. In combination these traits set 'Lady in Red' apart from all other existing varieties of *Physocarpus* known to the inventor.

3 Drawing Sheets

Genus: *Physocarpus.* Species: *opulifolius.*
Denomination: 'Lady in Red'.

BACKGROUND OF THE INVENTION

The present invention relates to a new and distinct cultivar of *Physocarpus,* or ninebark, that is grown for use as an ornamental landscape plant. It is known botanically as *Physocarpus opulifolius* and will be referred to hereinafter by the cultivar name 'Lady in Red'.

'Lady in Red' was discovered at the inventor's nursery in Norfolk, United Kingdom, in a batch of seedlings grown from seed collected by the inventor from *Physocarpus opulifolius* cultivar 'Monlo' (U.S. Plant Pat. No. 11,211) and sown in 2000.

'Lady in Red' was selected from the resulting population of seedlings or its distinguishing combination of red leaves and pink flowers. The closest cultivars known to the inventor are 'Monlo' and 'Diable d'Or' (unpatented), but both of those have creamy-white flowers. In addition, the emerging foliage of 'Diable d'Or' is amber in color compared to the red of 'Lady in Red'.

Asexual reproduction of 'Lady in Red' was first accomplished by the inventor in 2001, at the inventor's nursery in Norfolk, United Kingdom. The method of asexual propagation used was stem cuttings. Since that time the characteristics of the new cultivar have been determined stable and to be reproduced true to type in successive generations of vegetative propagation.

SUMMARY OF THE INVENTION

The following traits have been repeatedly observed and represent the characteristics of the new *Physocarpus* cultivar 'Lady in Red'. These traits in combination distinguish this cultivar from all other commercial varieties known to the inventor. 'Lady in Red' has not been tested under all possible conditions and phenotypic differences may be observed with variations in environmental, climatic and cultural conditions without however any difference in genotype.

1. *Physocarpus* 'Lady in Red' exhibits a free branching shrubby growth habit.
2. *Physocarpus* 'Lady in Red' exhibits red foliage.
3. *Physocarpus* 'Lady in Red' exhibits pink flowers.

4. *Physocarpus* 'Lady in Red' is 2 m in overall height and 2 m in width in a 1.5-liter container.
5. *Physocarpus* 'Lady in Red' is deciduous.
6. *Physocarpus* 'Lady in Red' blooms in mid-June.

BRIEF DESCRIPTION OF THE DRAWINGS

The accompanying color drawings illustrate the overall appearance of the new *Physocarpus* variety 'Lady in Red' showing colors as true as it is reasonably possible to obtain in colored reproductions of this type. Colors in the drawings may differ from the color values cited in the detailed botanical description, which accurately describe the actual colors of the new variety 'Lady in Red'.

The drawing labeled as FIG. 1 illustrates the entire plant in flower.

Figure 1:
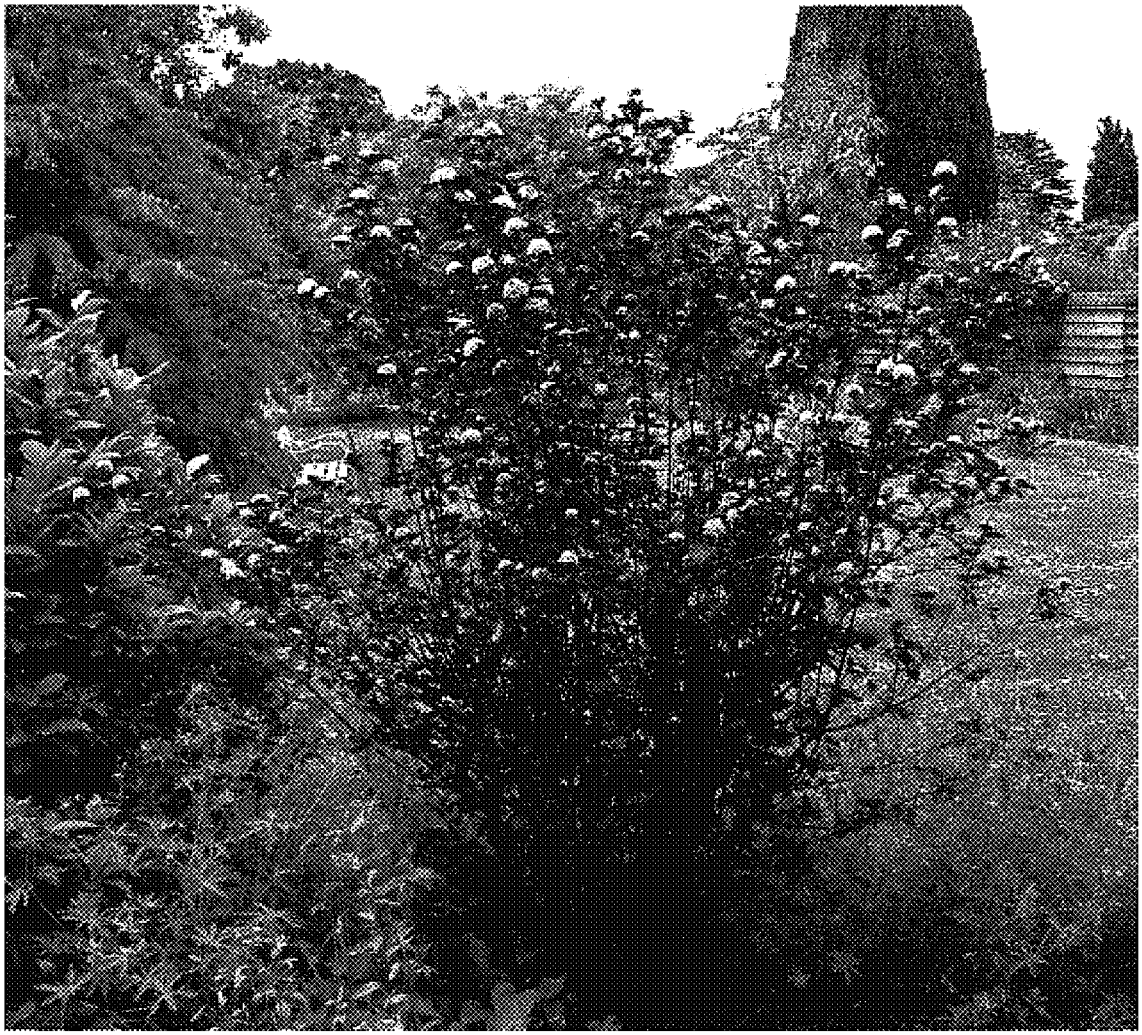
Figure 2:
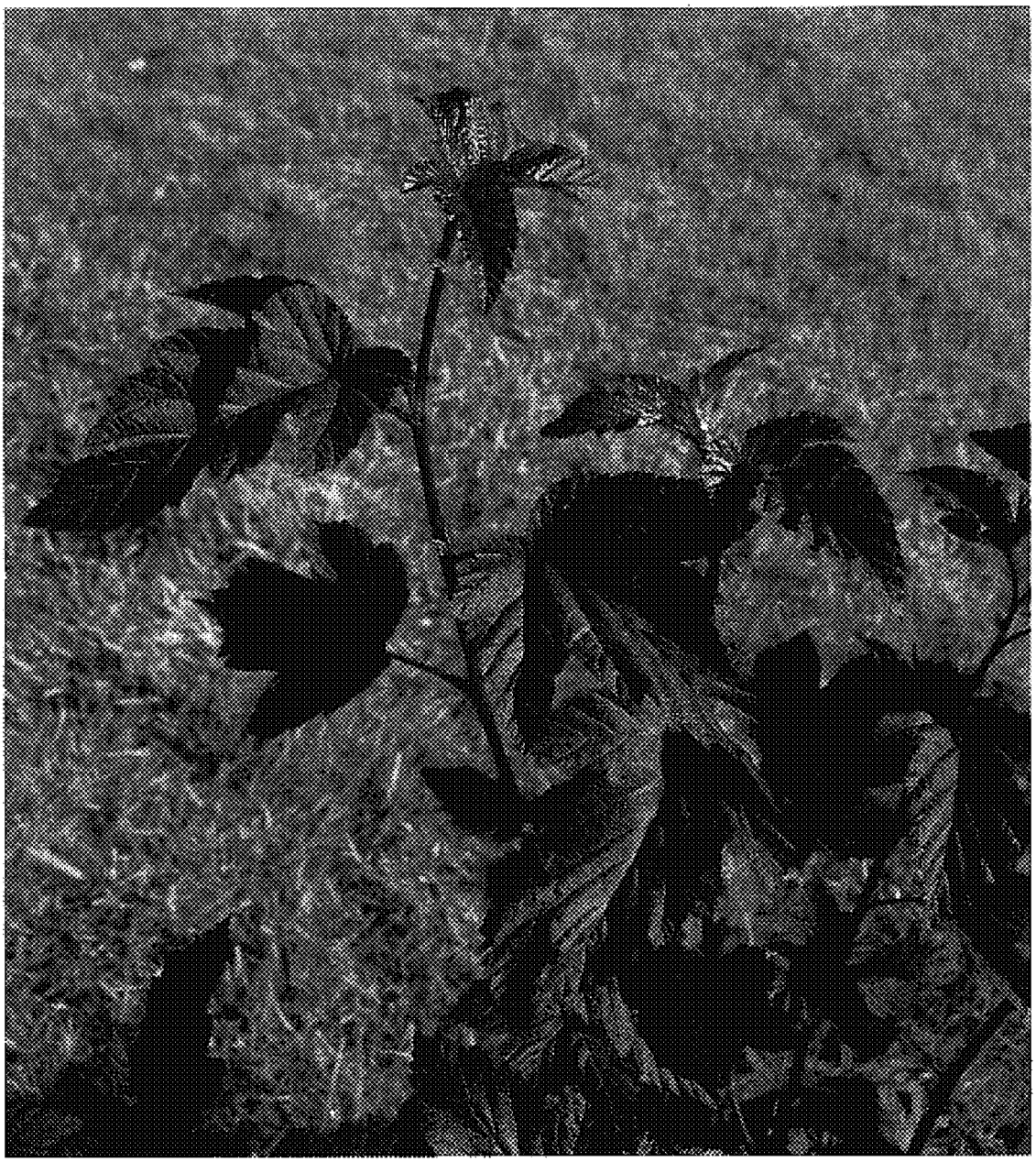

The drawing labeled as FIG. 2 illustrates the emerging foliage.

Figure 3:
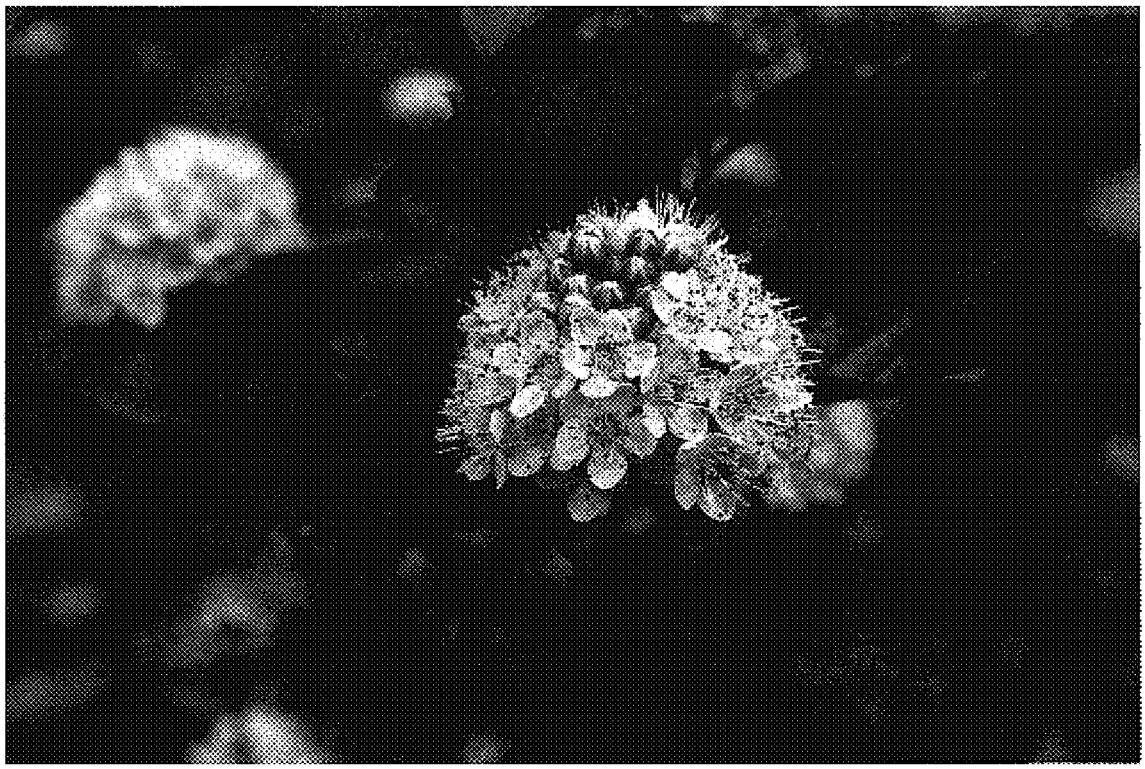

The drawing labeled as FIG. 3 illustrates a close up view of an inflorescence.

All drawings were made from 4 year old plants grown in open ground in Norfolk, England. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Lady in Red'. Data was collected from 2 year old plants grown out of doors in 1.5-liter containers in Norfolk, England. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions were typical to other *Physocarpus.*

Botanical classification: *Physocarpus opulifolius* 'Lady in Red'.
Genus: *Physocarpus.*
Species: *opulifolius.*

Common name: Ninebark.
Commercial classification: Deciduous shrub.
Use: Garden shrub.
Parentage: Open pollination of *Physocarpus* 'Monlo' (female parent).
Plant description:
*Bloom period.*—Mid-June.
*Plant habit.*—Freely branching shrub.
*Plant dimensions at maturity.*—2 m in overall height and width.
*Plant hardiness.*—USDA Zone 2.
*Type.*—Deciduous shrub.
*Root system.*—Fibrous.
*Propagation.*—Propagation is accomplished using softwood cuttings.
*Cultural requirements.*—Plant in full sun, well-drained and moderately fertile soil and keep well fertilized and watered. Soil pH preferably under 7.5.
*Diseases and pests.*—In common with *Physocarpus* generally, 'Lady in Red' is susceptible to aphid infestation. No other susceptibility or resistance to pests or diseases is known to the inventor.
*Time required to produce a rooted cutting.*—2 weeks.
*Temperature recommended for cuttings to produce roots.*—The air temperature needed is a minimum of 20° Centigrade air temperature.
*Crop time.*—18-24 months to produce a commercially saleable plant in a 1 gallon container.
Foliage:
*Main branch.*—Texture: Smooth, peeling. Lenticels: Absent. Color: Peeling bark 199D, exposed underlying bark 199C streaked with 200D. Diameter: 20 mm. Branching habit: Branching freely along the stems. Branch angle at emergence: 60°.
*Young stem.*—Color: 178A. Texture: Smooth. Pubescence: Absent. Lenticels: Absent. Cross-section: Weakly ribbed with a pithy-filled central cavity. Internode length: 50 mm. Diameter: 6 mm. Leaf arrangement: Alternate.
*Stipules.*—Presence: Present. Shape: Asymmetrically ovate with attenuate tip. Dimensions: 11 mm in length and 1.5 mm in width. Color: 177D.
*Petiole.*—Presence: Present. Dimensions: 23 mm in length, 1.5 mm in width. Pubescence: Absent. Color: 183A.
*Leaf.*—Shape: 3-lobed, overall shape broad ovate. Dimensions: 75 mm in length and 60 mm in width. Apex: Acute. Base: Weakly cordate. Thickness: Thin. Margins: Double-toothed, secondary teeth crenate. Emerging leaf color (adaxial): 183A, but more intense; veins same as lamina. Emerging leaf color (abaxial): Lamina N199A; mid-vein 176A; lateral veins as lamina. Mature leaf color (adaxial): Between 200A and N200A; veins as lamina. Mature leaf color (abaxial): Lamina nearest 194A, but browner and more intense; mid-vein 172B at base merging to 195B at tip; lateral veins 195B. Pubescence (adaxial and abaxial surfaces): Absent. Venation pattern: Pinnate. Fragrance: Absent.
Inflorescence:
*Flowering season.*—Mid-June in UK conditions.
*Inflorescence type.*—Dense terminal corymbs on short lateral branches. Corymb diameter: 50 mm. Approximate number of flowers per inflorescence: Between 50 to 100.
*Peduncle.*—Dimensions: 10 mm in length and 2 mm in diameter. Color: 178A. Pubescence: Absent.
*Pedicel.*—Dimensions: 13 mm in length and 0.5 mm in width. Color: 182C. Pubescence: Absent.
*Bud.*—Dimensions: 4 mm in length and diameter. Shape: Spherical. Color: 63C.
*Flowers.*—Flowers persistent or self-cleaning: Self-cleaning. Flower type: Single. Fragrance: Very weak. Shape: Salver-shaped. Dimensions: 5 mm in length and 10 mm in diameter. Aspect: Radiating from the center of the corymb. Note: Perianth segments and stamens arise from the margins of a cup-shaped hypanthium (floral cup). Hypanthium dimensions: 2 mm in length and 4 mm in diameter. Hypanthium color: 161A. Calyx dimensions: 8 mm in diameter; 0 mm in height as sepals are horizontal. Number of sepals: 5. Sepals: Dimensions: 3 mm in length, 2.5 mm in width. Shape: Triangular-ovate. Apex: Sharply acute. Margin: Smooth, flat. Pubescence: Upper and lower surfaces finely pubescent. Color: Outer surface 181B, inner surface 181D. Corolla: Shape: Salver-shaped. Number of petals/lobes: 5. Segments fused or free: Free. Depth of throat: Throat absent. Petal: Shape: Almost round (very broad ovate), concave. Tip: Rounded. Base: Rounded. Margin form: Smooth. Surface: Smooth. Dimensions: 5 mm in length and 4 mm in width. Color (outer surface): 73C. Color (inner surface): 75C.
Reproductive organs:
*Stamen number.*—25.
*Filament dimensions.*—5 mm in length and less than 0.5 mm in width.
*Filament color.*—155A.
*Anther dimensions.*—0.5 mm in length and less than 0.5 mm in width.
*Anther shape.*—Rounded rectangular.
*Anther color.*—N186B.
*Pollen color.*—4D.
*Pollen quantity.*—Small.
*Stigma number.*—5; 1 per follicle.
*Stigma shape.*—Capitate.
*Stigma diameter.*—0.5 mm.
*Stigma color.*—5C.
*Style shape.*—Filiform.
*Style dimensions.*—5 mm in length and less than 0.5 mm in width.
*Style color.*—155A.
*Ovary position.*—Superior.
*Ovary shape.*—A group of 5 follicles connate at the base.
*Ovary dimensions.*—1.5 mm in length and 2 mm in overall width.
*Ovary color.*—154C.
Seed:
*Number.*—2 per follicle.
*Shape.*—Ovoid, shiny.
*Dimensions.*—2 mm in length and 1 mm in width.
*Color.*—164B and 164C.

It is claimed:

1. A new and distinct cultivar of *Physocarpus* plant named 'Lady in Red' as described and illustrated herein.

* * * * *